United States Patent
Senin et al.

(10) Patent No.: US 10,799,376 B2
(45) Date of Patent: Oct. 13, 2020

(54) SYSTEMS AND METHOD FOR STENT MANUFACTURING USING PROTECTIVE SHIELDS

(71) Applicant: MEDINOL LTD., Tel Aviv (IL)

(72) Inventors: Vladlen Senin, Rishon LeZion (IL); Oded Stein, Kfar HaHoresh (IL)

(73) Assignee: Medinol Ltd., Tel Aviv (IL)

( * ) Notice: Subject to any disclaimer, the term of this patent is extended or adjusted under 35 U.S.C. 154(b) by 328 days.

(21) Appl. No.: 15/859,319

(22) Filed: Dec. 29, 2017

(65) Prior Publication Data
US 2019/0201221 A1 Jul. 4, 2019

(51) Int. Cl.
| | |
|---|---|
| A61F 2/915 | (2013.01) |
| B23K 26/22 | (2006.01) |
| B23K 31/02 | (2006.01) |
| B23K 26/282 | (2014.01) |
| B23K 101/06 | (2006.01) |

(52) U.S. Cl.
CPC .............. *A61F 2/915* (2013.01); *B23K 26/22* (2013.01); *B23K 26/282* (2015.10); *B23K 31/027* (2013.01); *A61F 2210/0014* (2013.01); *A61F 2220/0058* (2013.01); *A61F 2230/0069* (2013.01); *A61F 2240/00* (2013.01); *A61F 2240/001* (2013.01); *A61F 2240/002* (2013.01); *A61F 2250/0067* (2013.01); *B23K 2101/06* (2018.08)

(58) Field of Classification Search
CPC .............. A61F 2/915; A61F 2210/0014; A61F 2220/0058; A61F 2230/0069; A61F 2240/00; A61F 2240/001; A61F 2250/0067; A61F 2240/002; B23K 2101/06; B23K 31/027; B23K 26/22; B23K 26/282; B23K 2201/06
See application file for complete search history.

(56) References Cited

U.S. PATENT DOCUMENTS

| | | | | |
|---|---|---|---|---|
| 5,449,373 A | * | 9/1995 | Pinchasik | A61F 2/856 606/198 |
| 5,906,759 A | * | 5/1999 | Richter | A61F 2/91 219/121.63 |

(Continued)

FOREIGN PATENT DOCUMENTS

WO    WO 98/45506    10/1998

OTHER PUBLICATIONS

International Search Report and Written Opinion dated May 10, 2019 for PCT Application No. PCT/IB2018/001587, 12 pages.

*Primary Examiner* — Frederick C Nicolas
(74) *Attorney, Agent, or Firm* — Cadwalader, Wickersham & Taft LLP

(57) ABSTRACT

The present disclosure is directed to a stent manufacturing assembly including an inner shield, a patterned metal sheet, and an outer shield. The patterned metal sheet may include a polymer coating with an embedded therapeutic agent. The inner shield, patterned metal sheet, and outer shield are arranged in a layered configuration and placed in a stent rolling mechanism with a mandrel. In particular, the patterned metal sheet is disposed on the outer shield and the inner shield is disposed on the patterned metal sheet in the layered configuration. In the layered configuration, the stent manufacturing assembly is rolled by the rolling mechanism into a tubular shape and welded to form a tubular stent.

30 Claims, 13 Drawing Sheets

(56) References Cited

U.S. PATENT DOCUMENTS

| | | | | |
|---|---|---|---|---|
| 6,083,257 | A * | 7/2000 | Taylor | A61F 2/90 623/1.46 |
| 6,692,522 | B1 * | 2/2004 | Richter | A61F 2/91 623/1.15 |
| 7,208,009 | B2 | 4/2007 | Richter | |
| 8,037,733 | B2 * | 10/2011 | Banas | C23F 1/00 72/370.04 |
| 2003/0114918 | A1 | 6/2003 | Garrison et al. | |

\* cited by examiner

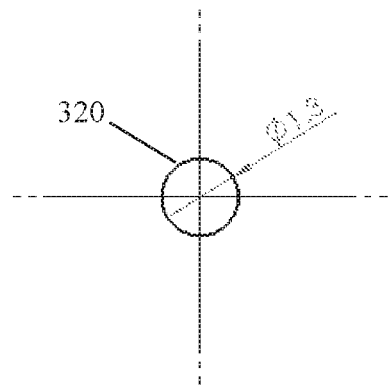
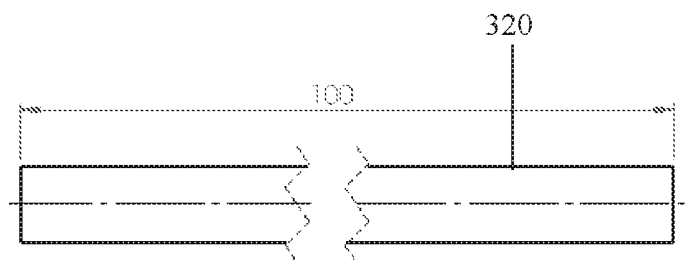
FIG. 3A          FIG. 3B
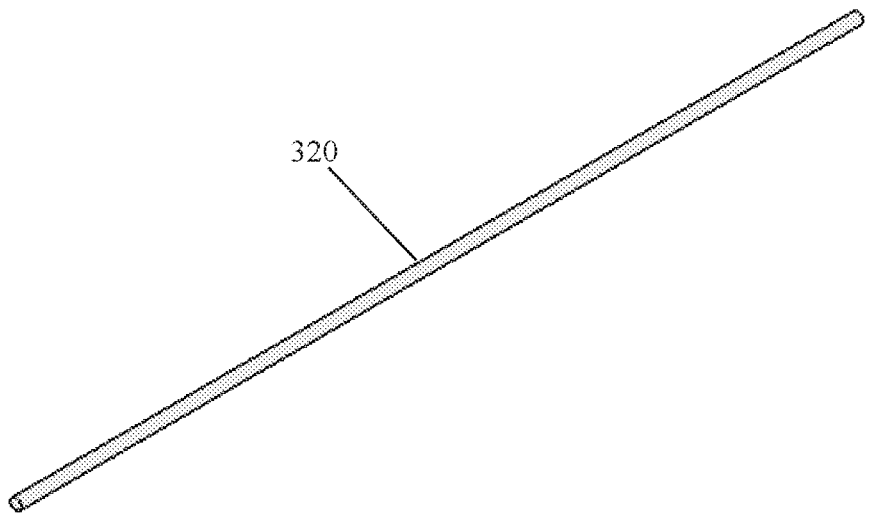
FIG. 3C

700

702 providing a stent manufacturing assembly comprising an outer shield having an outer cutout portion and an outer alignment portion, a patterned metal sheet disposed on the outer shield, said patterned metal sheet having a stent portion and a stent alignment portion; and an inner shield having an inner cutout portion and an inner alignment portion, said inner shield disposed on the patterned metal sheet 704 rolling the inner cutout portion, the stent portion, and the outer cutout portion around a mandrel 706 welding a first long edge of the stent portion to a second long edge of the stent portion to form a tubular stent; and 708 removing the tubular stent from the mandrel

FIG. 7

SYSTEMS AND METHOD FOR STENT MANUFACTURING USING PROTECTIVE SHIELDS

FIELD OF THE INVENTION

The present invention relates to a system and method for manufacturing a tubular stent from a patterned metal sheet. In particular, the present invention relates to a stent manufacturing assembly including an outer shield, a patterned metal sheet, and an inner shield. In addition, the invention relates to a system and method for rolling the assembly around a mandrel. and welding the rolled patterned metal sheet together to form the tubular stent.

BACKGROUND

In various medical procedures such as, for example, coronary angioplasty, a balloon is inflated within the lumen of a narrowed blood vessel at a target site in order to widen the vessel for improved blood flow. A tubular stent is then inserted at the target site to permanently hold open and support the vessel. The stent, which may be balloon expandable or self-expandable, as is well known in the art, is initially inserted in its relatively small, compressed state mounted on the end of a catheter, and the catheter is directed through the lumen of a vessel to the intended implantation site. After reaching its intended implantation site, the stent is expanded to a larger diameter to hold the vessel open.

One method of manufacturing a stent includes cutting a pattern into a metal tube using laser etching, such as the method described in U.S. Pat. No. 4,776,337. In this method, portions of a wall of a biocompatible metal tube are cut away such that the remaining material forms a mesh-like tube. This method requires that the pattern be cut into each tube individually, which is time consuming and inefficient. Another disadvantage is that the inner surface of the resulting stent cannot be adequately inspected, and defects on this surface are incorporated into the final stent. Any defects compromise the integrity of the stent and thus increase the risk of medical device failure.

In another method of stent manufacturing, a mandrel is employed in order to fold a sheet of metal, for example, into a tubular shape. In this method, a plurality of stent patterns is laser-cut onto a sheet in a single step. The individual stent patterns can be easily inspected on both sides of the sheet before folding the sheet into a stent. Each pattern is then deformed around a cylindrical mandrel such that each pattern is forced to take on the shape of the mandrel. The edges of the pattern are then brought together and welded, the mandrel is removed, and a tubular stent having the pattern that provides the desired strength and flexibility is the resulting product. The method employing a mandrel is considered advantageous to other methods, because (1) a pattern can be easily cut into a flat sheet, (2) both sides of the patterned sheet can be inspected prior to deformation, and (3) the method is highly efficient.

However, one problem with the method employing a mandrel is that the contact between the mandrel and the internal surface of the patterned sheet (the stent), during removal of the mandrel, can result in damage to the internal surface of the sheet. In addition, stents are often coated with a special polymer, a drug, or a combination thereof. Deformation of the sheet and removal of the mandrel can cause damage to the integrity of the coated surface material by the contact, friction, and/or pressure between the mandrel and the inner surface of the stent.

In view of the foregoing, there exists a need to provide a stent manufacturing assembly and method for protecting the internal surface of the stent and the outer surface of the mandrel during the stent manufacturing process.

SUMMARY OF THE INVENTION

A stent manufacturing assembly of the present invention includes (1) an outer shield having a cutout portion and an alignment portion, (2) a patterned metal sheet having a first (abluminal) side, a second (luminal) side, and a thickness therebetween, wherein the first side of the patterned metal sheet is positioned on the outer shield, and (3) an inner shield having a cutout portion and an alignment portion positioned on the second side of the patterned metal sheet. The stent manufacturing assembly may further include a mandrel.

In an embodiment, the patterned metal sheet may include an alignment portion and a cutout portion that is a laser-cut stent pattern. The alignment portion may include one or more alignment holes. The patterned metal sheet may optionally include a coating. The coating may be a therapeutic agent or a material to facilitate release of a therapeutic agent. The therapeutic agent may inhibit proliferation of smooth muscle cells.

Another aspect of the invention relates to a method of manufacturing a stent using a stent manufacturing assembly comprising an outer shield having an alignment portion and a cutout portion, a patterned metal sheet having an alignment portion and a cutout portion, and an inner shield having an alignment portion and a cutout portion. The method may include the steps of positioning the first side of the patterned metal sheet on the outer shield and positioning the inner shield on the second side of patterned metal sheet, rolling the cutout portion of the inner shield, the cutout portion of the patterned metal sheet, and the cutout portion of the outer shield around a mandrel, welding a first long edge of the cutout portion of the patterned metal sheet to a second long edge of the cutout portion of the patterned metal sheet to form a tubular stent, removing the outer shield from the stent manufacturing assembly, and removing the tubular stent from the mandrel. The method may optionally include the additional step of removing the inner shield from the mandrel either concurrently with the tubular stent or after the tubular stent has been removed.

In an embodiment, the method further includes loading the stent manufacturing assembly into a stent rolling mechanism. In an embodiment, the method further includes aligning the alignment holes with one or more alignment pins on the stent rolling mechanism.

BRIEF DESCRIPTION OF THE DRAWINGS

The present invention will be understood and appreciated more fully from the following detailed description taken in conjunction with the drawings in which:

FIG. 3A-3C show a mandrel used to manufacture a stent.

FIG. 7 shows a flow diagram for a method of manufacturing a stent using a stent manufacturing assembly.

DETAILED DESCRIPTION OF THE INVENTION

Figure 1:
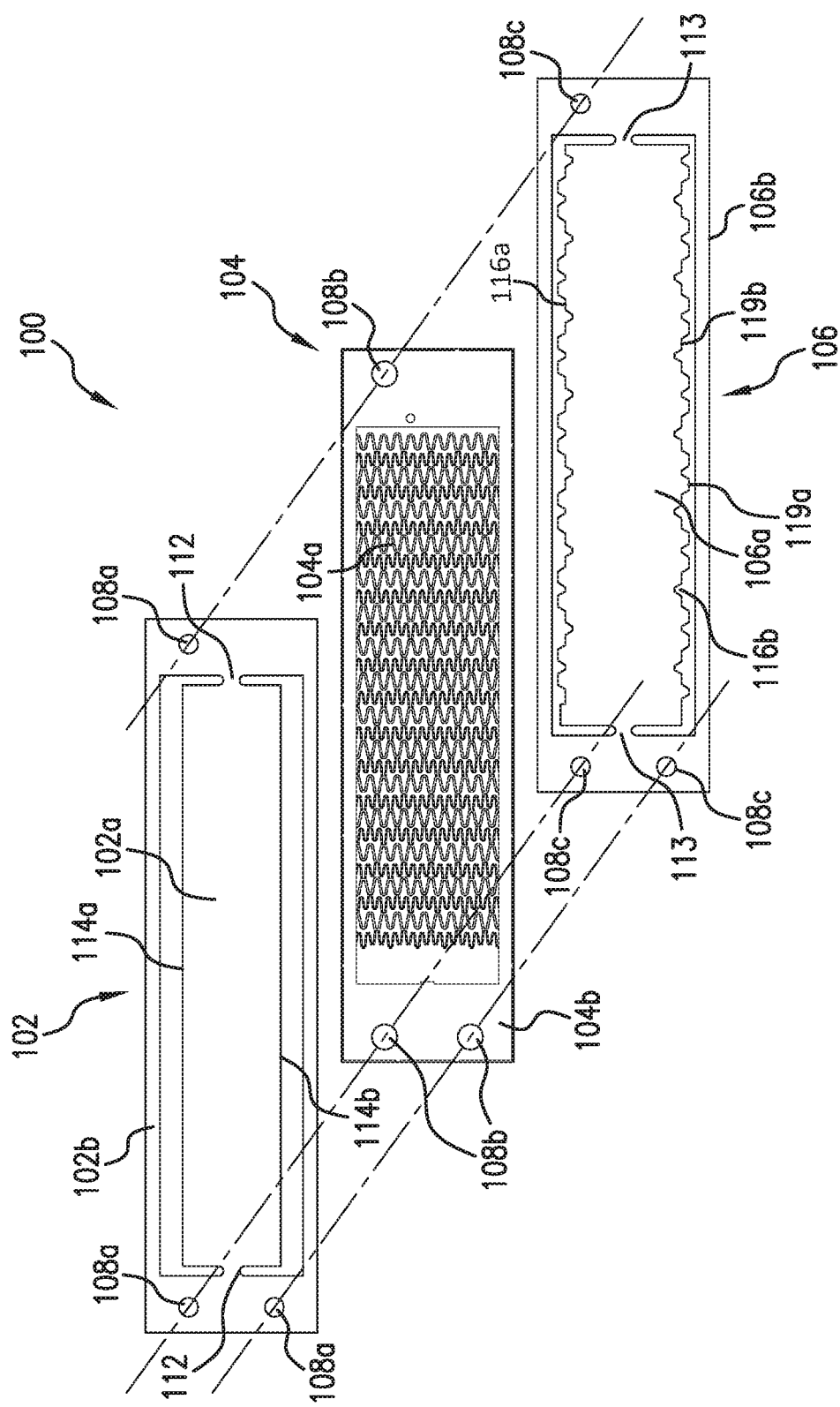
FIG. 1 shows a stent manufacturing assembly including an inner shield, a patterned metal sheet, and an outer shield.

A stent manufacturing assembly of the invention generally includes an outer shield, a patterned metal sheet, and an inner shield. The inner shield and the outer shield may be disposable after a tubular stent is formed from rolling and welding the patterned metal sheet. The stent manufacturing assembly is arranged such that the patterned metal sheet is disposed on the outer shield such that the outer shield contacts a first side of the patterned metal sheet. The inner shield is disposed on the patterned metal sheet such that the inner shield contacts a second side of the patterned metal sheet (opposite the first side) in a layered configuration during the stent manufacturing process. In this layered configuration, one or more alignment holes may be used to align each of the outer shield, patterned metal sheet, and inner shield.

The outer shield includes a cutout portion that is configured to protect a first side (i.e., the outer surface) of the patterned metal sheet from, e.g., contact with the stent rolling mechanism, during manufacture and an outer alignment portion. The inner and outer alignment portions have inner and outer alignment holes and are configured to align the outer shield, the patterned metal sheet, and the inner shield when in the layered configuration in the stent manufacturing process. The outer shield may further include at least two outer tabs connecting the outer cutout portion to the outer alignment portion. The outer tabs may be configured to be cut or torn to separate the outer cutout portion from the outer alignment portion during the stent manufacturing process.

The cutout portion of the outer shield may include a first long edge and a second long edge that have a toothed or jagged configuration along the longitudinal length of the outer cutout portion. When the cutout portion of the outer shield is folded around the patterned metal sheet, some portions of the first long edge may meet the second long edge along the length of the outer cutout portion while other portions along the length of the outer cutout portion may include gaps between the first long edge and the second long edge. The gaps between the first long edge and the second long edge may provide, for example, access to portions of the patterned metal sheet for injection of argon gas, illumination, and laser welding, inter alia, at specific weld zones. The gaps in the jagged configuration may correspond to a position at which a valley in the first long edge meets a valley of the second long edge in the outer cutout portion. Likewise, the first long edge may meet the second long edge at a location (or locations) along the length of the first and second long edges where a peak on the first long edge aligns with a peak on the second long edge. The term "jagged" is defined as having protrusions (or peaks) and recesses (or valleys) along a longitudinal length of an edge. The protrusions and recesses may be spaced from each other in a repeating pattern along the length of the edge.

The alignment portion of the outer shield includes one or more alignment holes. The alignment hole(s) may be used to align the outer shield with the patterned metal sheet and inner shield by inserting an alignment pin through the alignment hole(s). This step of aligning the stent manufacturing assembly may occur when the inner shield, patterned metal sheet, and outer shield are positioned on the stent rolling mechanism such that alignment pin(s) pass through the alignment hole(s).

The inner shield includes a cutout portion that is configured to protect a luminal side of the patterned metal sheet from, e.g., a mandrel, during stent manufacture and an inner alignment portion configured to align the inner shield with the patterned metal sheet and the outer shield when in the layered configuration in the stent manufacturing process. The inner shield may further include at least two inner tabs connecting the cutout portion of the inner shield to the inner alignment portion of the inner shield. The inner tabs may be configured to be cut or torn to separate the cutout portion from the alignment portion during the stent manufacturing process. After the flat metal sheet is rolled into a tubular stent and welded, the inner shield may be removed from the mandrel concurrently with the tubular stent or after the tubular stent has been removed.

The cutout portion of the inner shield may include a first long edge and a second long edge both of which are parallel to the longitudinal axis of the mandrel. When the cutout portion of the inner shield is folded around a mandrel, the first long edge may meet the second long edge. Alternatively, there may be a gap between the first long edge and the second long edge of a predefined distance when the cutout portion is wrapped around a mandrel.

The alignment portion of the inner shield includes one or more alignment holes. The alignment holes may be used to align the inner shield with the patterned metal sheet and outer shield by inserting an alignment pin through each of the alignment holes. This step of aligning the stent manufacturing assembly may occur when the assembled inner shield, patterned metal sheet, and outer shield are positioned on the stent rolling mechanism.

Similarly, the cutout portion of the inner shield may include a first long edge and a second long edge that have a substantially parallel configuration. When the cutout portion of the inner shield is folded around the mandrel, the first long edge may contact the second long edge. Alternatively, the first long edge may be spaced away from the second long edge by a predefined distance when the cutout portion of the inner shield is wrapped around the mandrel.

The patterned metal sheet includes a sheet alignment portion configured to align the patterned metal sheet with the inner shield and the outer shield, so that the stent portion of the patterned metal sheet is aligned with the inner and outer cutout portions. As stated above, a stent pattern may be formed in the metal sheet using techniques such as, for example, chemical or laser etching, laser-cut, or other methods known in the art. The patterned metal sheet may include metals such as, e.g., stainless steel, a shape-memory alloy such as Nitinol, platinum chromium alloy, cobalt chromium alloy, or other suitable biocompatible metal or metal alloy.

The stent manufacturing assembly facilitates formation of a stent from a patterned metal sheet according to various known methods. One non-limiting example of such method is described in U.S. Pat. No. 7,208,009, which is hereby incorporated by reference in its entirety. In this method, a patterned metal sheet is deformed into the cylindrical shape of a mandrel, and the edges of the sheet are then joined (by welding, for example) to form a stent. Preparation and cutting of such flat patterned metal sheet designs are shown, for example, in U.S. Pat. Nos. 6,692,522, and 5,906,759, that are both incorporated by reference in their respective entireties. Other similar manufacturing methods are known to the skilled person and are understood to be within the scope of the invention.

The patterned metal sheet may optionally include a coating with an embedded therapeutic agent, where the coating is applied to the first (abluminal) side and/or the second (luminal) side of the patterned metal sheet. In an embodiment, the coating may be applied to both sides, or in an alternative embodiment, the coating may be applied to one side and not the other side. In an example, the coating may be a polymer coating including one or more therapeutic agents or materials. For example, the therapeutic agent may be an anti-infective, anti-inflammatory, an immunosuppressive, cytostatic, cytotoxic, and/or an antiproliferative agent. Alternatively, or additionally thereto, a material which facilitates or controls release of a therapeutic agent may be included in a coating. Such materials include polymers, sprays, nanoparticles, composites, and/or other suitable release control materials as is known in the art. In the embodiment where both the first side and the second side of the patterned metal sheet are coated, both an inner shield and an outer shield may be used to protect the coating during the stent manufacturing process.

The patterned metal sheet may be coated with, for example, a polymer and a therapeutic agent while the sheet is flat (i.e., prior to rolling) but after a pattern is cut into the sheet. The coating may be applied either before or after polishing (or electropolishing) the stent. There are many advantages of coating the patterned metal sheet in the flat configuration. For example, better uniformity of the therapeutic agent along the inner stent surface and/or outer stent surface may be achieved. The uniformity of coating a stent using techniques such as spraying or evaporation is much higher and easier to achieve with flat surfaces than it is with cylindrical surfaces of finished stents.

Various therapeutic agent and material coatings can be utilized with the present invention. For example, the drug coatings or drug and polymer coating combinations that are used to deliver the drug may include: antiproliferative/antimitotic agents including natural products such as vinca alkaloids (i.e. vinblastine, vincristine, and vinorelbine), paclitaxel, epidipodophyllotoxins etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as vitronectin receptor antagonists; antiproliferative/antimitotic alkylating agents such as nitrogen mustards (mechlorethamine, cyclophosphamide and analogs, melphalan, chlorambucil), ethylenimines and methyl-melamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6.alpha.-methylprednisolone, triamcinolone, betamethasone, and dexamethasone), bisphosphonates, non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), sirolimus analogues (e.g., ridaforolimus, everolimus, zotarolimus), aza-thioprine, mycophenolate mofetil); angiogenic agents: vascular endothelial growth factor (VEGF), fibroblast growth factor (FGF) platelet derived growth factor (PDGF), erythropoetin, angiotensin receptor blocker; nitric oxide donors; anti-sense oligonucleotides and combinations thereof; cell cycle inhibitors, mTOR inhibitors, and growth factor signal transduction kinase inhibitors. The flat metal panels are coated with one or more of the drug coatings or drug and material coating combinations. Other substances, such as bisphosphonates, can be used with the present invention, as described in U.S. Pat. No. 7,008,645 to Golomb et al., which is incorporated by reference in its entirety.

Material coatings can include, but are not limited to certain polymers, e.g., poly(glycol methacrylate), poly(methyl methacrylate), poly(ethyl methacrylate), poly(butyl methacrylate), poly(sulfanato ethyl methacrylate), poly(ethylene-co-vinyl acetate), poly(ethyl acrylate), poly(urethane-acrylate), poly(acrylamide-co-ethyl methacrylate), poly(divinyl benzene), poly(triethylene glycol-co-divinyl ether), poly(tri-methylol propane triacrylate), poly(pentaerythritol tetraacrylate), poly(Bisphenol A ethoxylate diacrylate), poly (allyl ether), poly(diallyl maleate), poly(vinylidene fluoride), poly(triallyl isocyanurate), poly (lactic acid), silicone, polycarbonate, urethane, and blends thereof. Other polymers used in the coating, for example, may be found in U.S. Pat. No. 6,673,386 to Ding, incorporated by reference in its entirety.

Alternatively, material coatings can include non-polymer materials such as, for example, metallic, chemical, and/or lubricative.

The inner shield and the outer shield may be made of a flexible material, such as a polymer. In an embodiment, the polymer may be polytetrafluoroethylene (PTFE), silicon, polyamide (PA), polyethylene terephthalate (PET), polyethylene (PE), polypropylene (PP), or any other suitable polymer as is known in the art. The inner shield and the outer shield may be made using techniques such as 3D printing, molding, cutting pieces from a flat sheet, or any other suitable manufacturing technique.

The mandrel may have a diameter between about 0.5 mm and about 5 mm. In another embodiment, the mandrel may have a diameter between about 1.2 mm and about 1.4 mm. In yet another embodiment, the mandrel may have a diameter of about 1.3 mm. The mandrel may have a length between about 50 mm and about 200 mm. In another embodiment, the mandrel may have a length between about 90 mm and about 110 mm. In yet another embodiment, the mandrel may have a length of about 100 mm. Throughout this disclosure, the term "about" is intended to indicate the allowance of error in the measurement up to plus or minus 10% of the specified value. The mandrel may include materials such as, for example, platinum, gold, stainless steel, a platinum-iridium alloy or other suitable metal for stent rolling and welding.

The stent manufacturing assembly may be aligned on a stent rolling device with one or more alignment pins. The stent manufacturing assembly may include the inner shield, patterned metal sheet, and outer shield in a layered configuration. In particular, the patterned metal sheet may be disposed on the outer shield and the inner shield may be disposed on the patterned metal sheet in a layered configuration. When the stent manufacturing assembly is placed in the stent rolling mechanism, the one or more alignment holes of the stent manufacturing assembly are aligned with one or more alignment pins of the stent rolling mechanism. The alignment pins and corresponding alignment holes constrain the stent manufacturing assembly from moving during the rolling and welding of the patterned metal sheet into a tubular stent. In particular, when the alignment pins are inserted into the alignment holes, the stent manufacturing assembly (i.e., the inner shield, outer shield, and patterned metal sheet) is constrained from lateral motion.

The stent rolling mechanism may further include grooves that are configured to hold the mandrel securely in place while the stent manufacturing assembly is rolled and welded. In the event that the groove is too large, a tube may be positioned over the mandrel on either end to increase the diameter of the mandrel so that the mandrel will tightly fit into the groove. The tube may be made of, for example, polytetrafluoroethylene (PTFE) or another suitable polymer or metal.

The invention further relates to a method of manufacturing a stent using a stent manufacturing assembly which may include providing stent manufacturing assembly comprising a patterned metal sheet having a sheet alignment portion and a stent portion, an inner shield having an inner alignment portion and a cutout portion, and an outer shield having an outer alignment portion and an outer cutout portion. The patterned metal sheet may be positioned on the outer shield such that the outer shield contacts a first (abluminal) side of the patterned metal sheet to protect the first side of the patterned metal sheet from contacting a stent rolling mechanism. The inner shield may be positioned on the patterned metal sheet such that the inner shield contacts a second (luminal) side of the patterned metal sheet to protect the second side from contact with a mandrel. The stent manufacturing assembly may be loaded into the stent rolling mechanism by aligning alignment hole(s) in the stent manufacturing assembly with alignment pin(s) in the stent rolling mechanism.

The cutout portion of the inner shield, the stent portion of the patterned metal sheet, and the cutout portion of the outer shield may be rolled around the mandrel sequentially or simultaneously. A first long edge of the stent portion of the patterned metal sheet may be welded to a second long edge of the stent portion of the patterned metal sheet to form a tubular stent. The first long edge may be welded at specific weld zones or in its entirety to the second long edge. The outer shield may be removed from the stent manufacturing assembly. Lastly, the tubular stent is removed from the mandrel.

FIG. 1 shows the components of a stent manufacturing assembly 100 i.e., an inner shield 102, a patterned metal sheet 104, and an outer shield 106. The inner shield 102 and the outer shield 106 may be disposable after a tubular stent is formed from rolling the assembly 100. The stent manufacturing assembly 100 is arranged such that the outer shield 106 contacts a first (abluminal) side of the patterned metal sheet 104 and the inner shield 102 contacts a second (luminal) side of the patterned metal sheet 104 forming a layered configuration during the stent manufacturing process. In this layered configuration, one or more inner alignment holes 108a, sheet alignment holes 108b, and outer alignment holes 108c may be used to align each of the inner shield 102, patterned metal sheet 104, and outer shield 106.

The inner shield 102 includes an inner cutout portion 102a and an inner alignment portion 102b. The inner shield 102 may further include at least two inner tabs 112 connecting the inner cutout portion 102a to the alignment portion 102b and the tabs 112 may be configured to be cut or torn to separate the inner cutout portion 102a from the inner alignment portion 102b during the stent manufacturing process.

The inner cutout portion 102a may include a first long edge 114a and a second long edge 114b that are substantially parallel to the longitudinal axis of the inner cutout portion 102a. When the inner cutout portion 102a is folded around a mandrel, the first long edge 114a may meet the second long edge 114b. Alternatively, there may be a space between the first long edge 114a and the second long edge 114b at a predefined distance when the inner cutout portion 102a is wrapped around the mandrel.

The inner alignment portion 102b includes inner alignment holes 108a. The inner alignment holes 108a may be used to align the inner shield 102 with the patterned metal sheet 104 and outer shield 106 by inserting an alignment pin through each of the inner alignment holes 108a, sheet alignment holes 108b, and outer alignment holes 108c. This step of aligning the stent manufacturing assembly may occur when the inner shield 102, patterned metal sheet 104, and outer shield 106 are placed on the stent rolling mechanism. In a preferred embodiment, two alignment holes are used. In a second embodiment, three alignment holes are used. In yet another embodiment, three, four, or five alignment holes are utilized. Additional alignment holes may also be employed in the invention.

The outer shield 106 includes an outer cutout portion 106a that is configured to protect a second side of the patterned metal sheet 104 from, e.g., contact with the stent rolling mechanism, during manufacture and an outer alignment portion 106b configured to align the outer shield 106 with the patterned metal sheet 104 and the inner shield 102 when in the layered configuration in the stent rolling mechanism. The outer shield 106 may further include at least two outer tabs 113 connecting the outer cutout portion 106a to the outer alignment portion 106b. The outer tabs 113 may be configured to be cut or torn to separate the outer cutout portion 106a from the outer alignment portion 106b during the stent manufacturing process.

The outer cutout portion 106a may include a first long edge 116a and a second long edge 116b that have a toothed or jagged configuration along the longitudinal length of the outer cutout portion 106a. When the outer cutout portion 106a is folded around the patterned metal sheet 104, some portions 119a of the first long edge 116a may meet the second long edge 116b along the length of the outer cutout portion 106a while other portions 119b along the length of the outer cutout portion 106a may include gaps between the first long edge 116a and the second long edge 116b. The gaps between the first long edge 116a and the second long edge 116b may provide, for example, access to portions of the patterned metal sheet 104 for injection of argon gas, illumination, and laser welding at specific weld zones.

The outer alignment portion 106b includes outer alignment holes 108c. The outer alignment holes 108c may be used to align the outer shield 106 with the patterned metal sheet 104 and inner shield 102 by inserting an alignment pin through each of the inner alignment holes 108a, sheet alignment holes 108b, and outer alignment holes 108c. This step of aligning the stent manufacturing assembly may occur when the inner shield 102, patterned metal sheet 104, and outer shield 106 are placed on the stent rolling mechanism such that alignment pins pass through the inner alignment holes 108a, sheet alignment holes 108b, and outer alignment holes 108c.

The inner shield 102 and the outer shield 106 may be made of a flexible material, such as a polymer. In an embodiment, the polymer may be polytetrafluoroethylene (PTFE), silicon, polyamide (PA), polyethylene terephthalate (PET), polyethylene (PE), polypropylene (PP), or any other suitable polymer as is known in the art. The inner shield and the outer shield may be made using techniques such as 3D printing, molding, cutting pieces from a flat sheet, or any other suitable manufacturing technique.

The patterned metal stent 104 includes a stent portion 104a that includes a stent pattern and a sheet alignment portion 104b configured to align the patterned metal sheet 104 with the inner shield 102 and the outer shield 106. As stated above, the stent pattern may be formed into the metal sheet using techniques such as, for example, laser cutting or chemical etching. The metal sheet may include stainless steel, a shape-memory alloy such as Nitinol, platinum chromium alloy, cobalt chromium alloy, or other suitable biocompatible metal or metal alloy.

The patterned metal sheet 104 may include a coating with an embedded therapeutic agent, where the coating is applied to the first side and/or the second side of the patterned metal sheet 104. In an example, the coating may be a polymer coating and the therapeutic agent may be an immunosuppressive drug and/or an antiproliferative drug. In the embodiment where both the first side and the second side of the patterned metal sheet 104 are coated with the therapeutic agent coating, both an inner shield 102 and an outer shield 106 may be used to protect the therapeutic agent coating(s) during the stent manufacturing process.

Figure 2A:
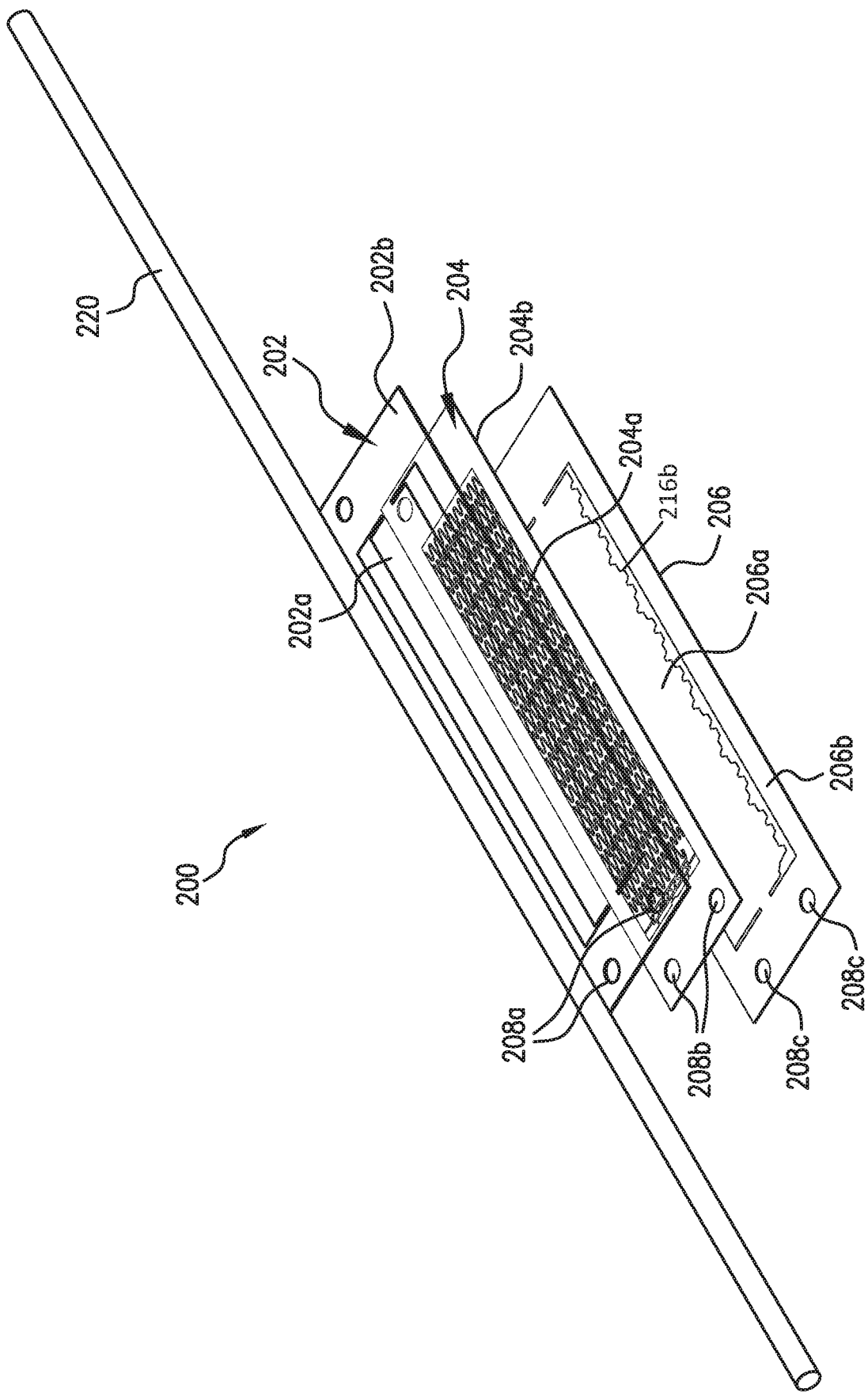
FIG. 2A shows a first step in manufacturing a stent using a stent manufacturing assembly including an inner shield, a patterned metal sheet, an outer shield, and a mandrel.

FIG. 2A shows a first step in manufacturing a stent using a stent manufacturing assembly 200 including an inner shield 202, a patterned metal sheet 204, an outer shield 206, and a mandrel 220. In particular, the inner shield 202, the patterned metal sheet 204, and the outer shield 206 are stacked on top of one another to align one or more inner alignment holes 208a, sheet alignment holes 208b, and outer alignment holes 208c through which alignment pins of a stent rolling mechanism (described in more detail below) will pass. The mandrel 220 may include materials known in the art such as, for example, platinum, gold, stainless steel, a platinum-iridium alloy, copper, or other suitable metals for stent rolling and welding.

Figure 2B:
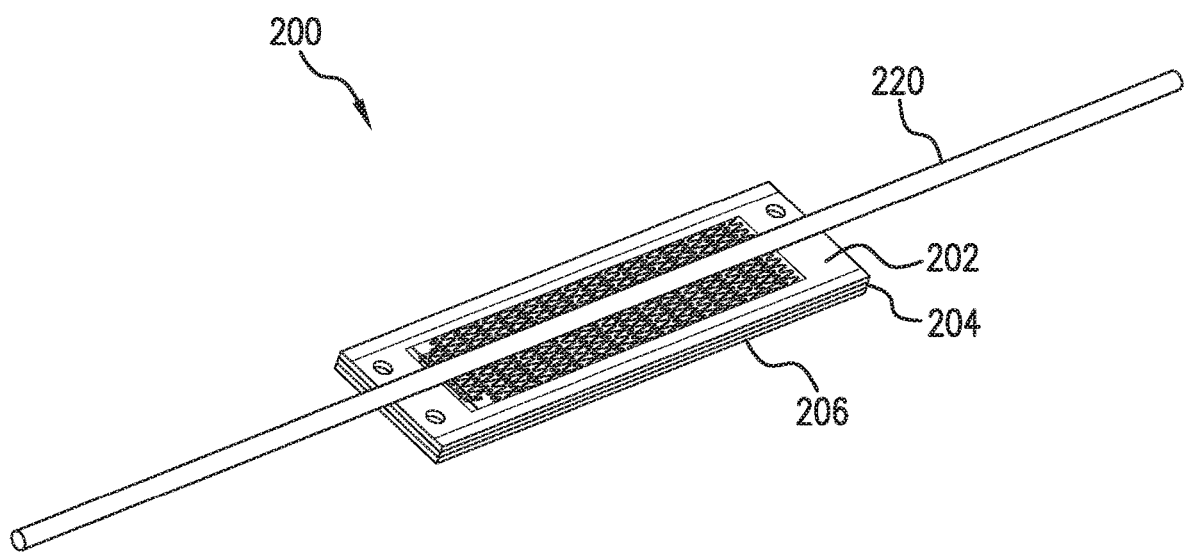
FIG. 2B shows a second step in manufacturing a stent using a stent manufacturing assembly where the inner shield, the patterned metal sheet, and the outer shield are aligned and stacked.

FIG. 2B shows a next step in manufacturing a stent using a stent manufacturing assembly 200 where the inner shield 202, the patterned metal sheet 204, and the outer shield 206 are aligned and stacked with the mandrel 220. In particular, the inner shield 202 is in contact with the mandrel 220, the second (luminal) side of the patterned metal sheet 204 is in contact with the inner shield 202, and the first (abluminal) side of the patterned metal sheet 204 is in contact with the outer shield 206 when the outer shield is used in the stent manufacturing assembly.

Figure 2C:
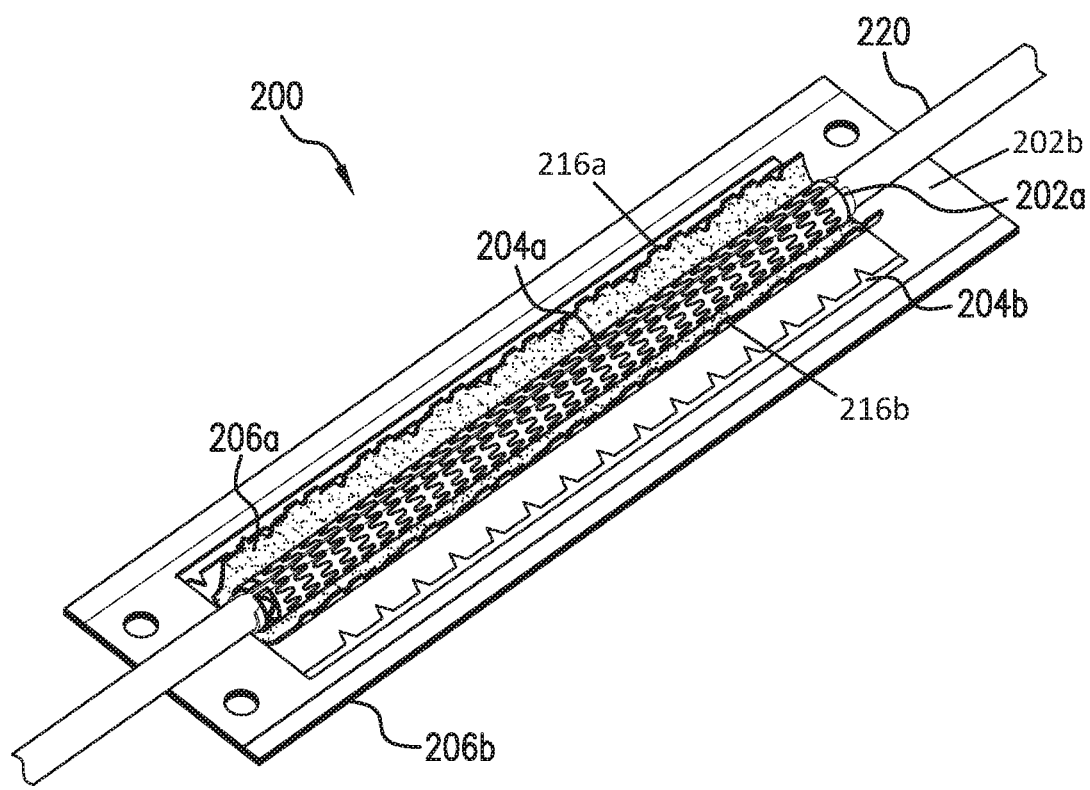
FIG. 2C shows another step in manufacturing a stent using a stent manufacturing assembly where the inner shield, the patterned metal sheet, and the outer shield are wrapped around the mandrel.

FIG. 2C shows a further step in manufacturing a stent using a stent manufacturing assembly 200 where the inner shield 202, the patterned metal sheet 204, and the outer shield 206 are wrapped around the mandrel 220. In particular, the inner cutout portion 202a, the stent portion 204a, and the outer cutout portion 206b are folded around the mandrel 220 while the inner alignment portion 202b, the stent sheet alignment portion 204b, and the outer alignment portion 206b remains stationary in, for example, a stent rolling mechanism.

Figure 2D:
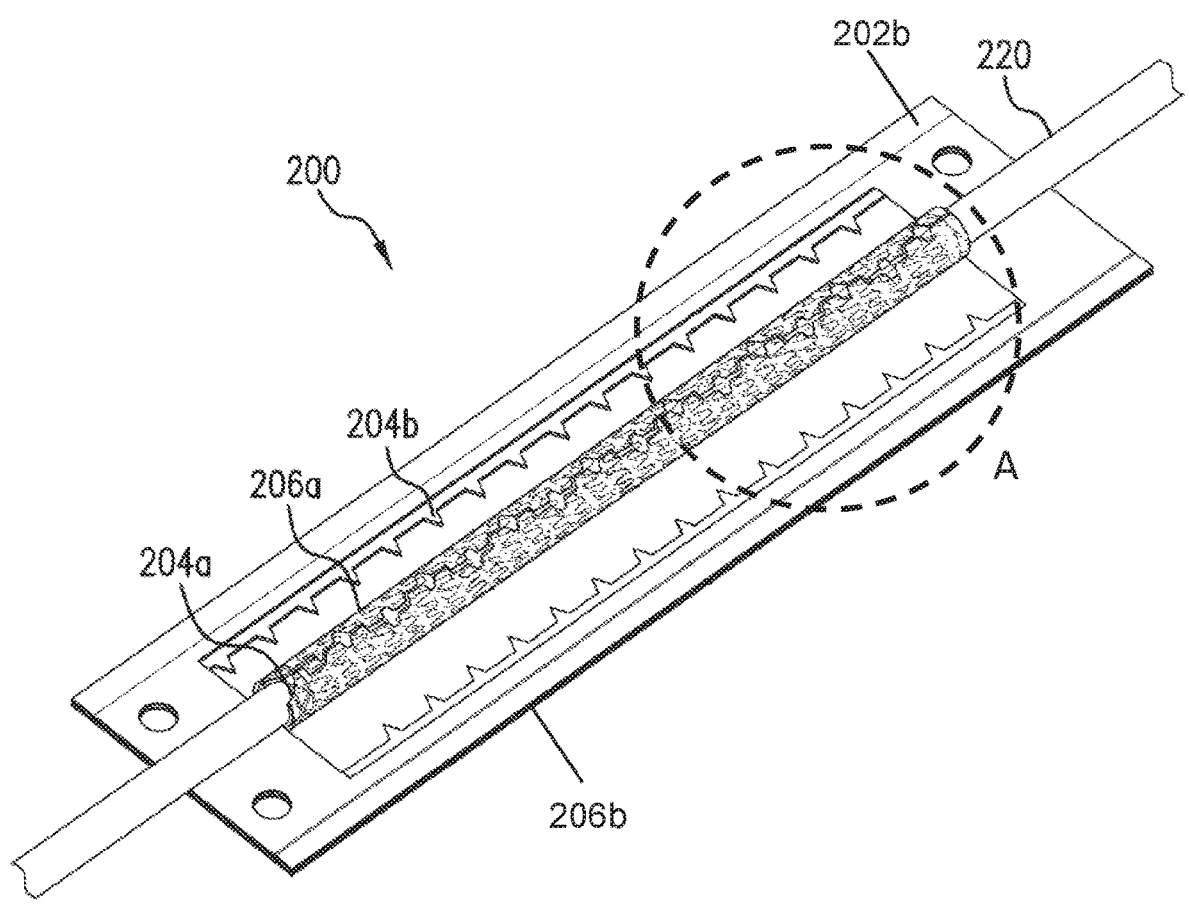
FIG. 2D shows yet another step in manufacturing a stent using a stent manufacturing assembly where the patterned metal sheet is welded to form a tubular stent.
Figure 2E:
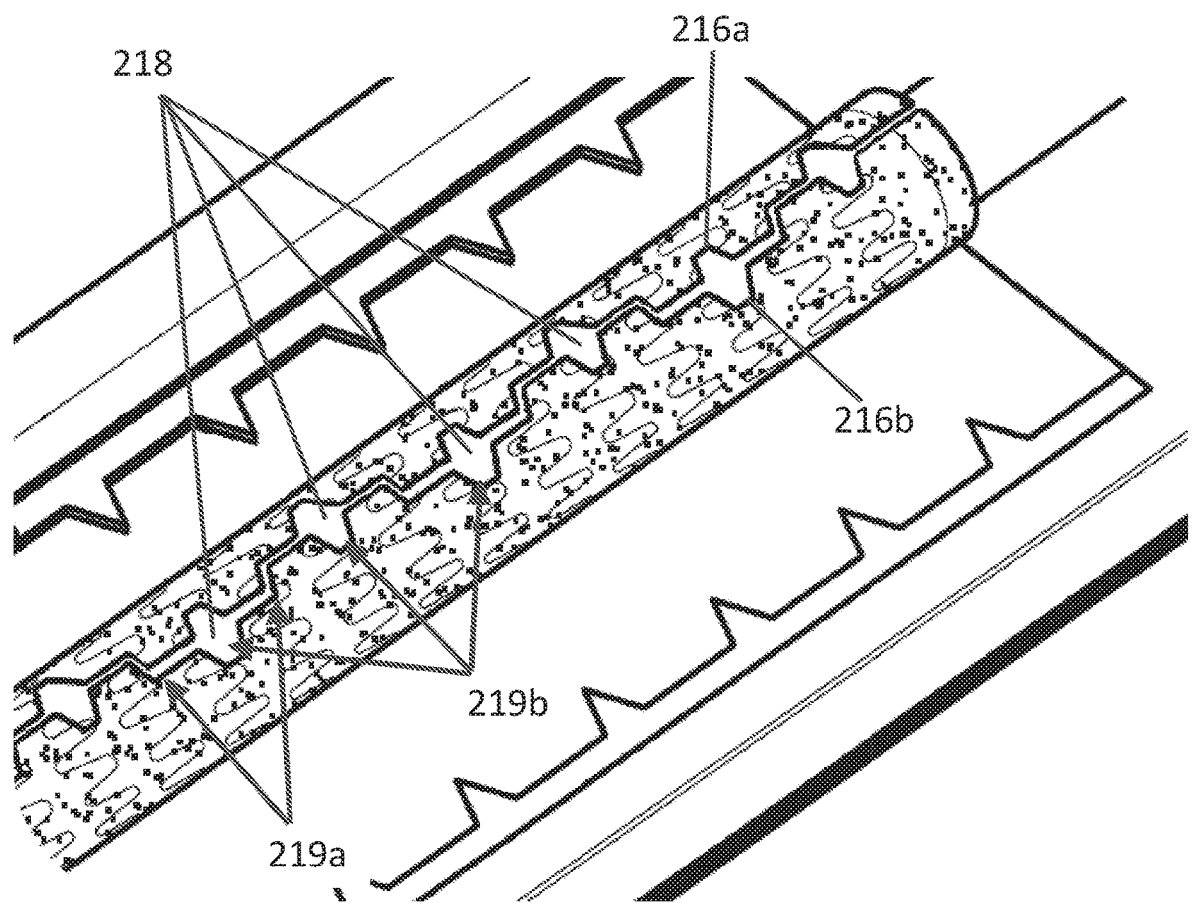
FIG. 2E shows a close-up view of section A identified in FIG. 2D.

FIGS. 2D and 2E show another step in manufacturing a stent using a stent manufacturing assembly 200 where the patterned metal sheet 204 is welded to form a tubular stent. In particular, FIG. 2E is a close-up view of section A identified in FIG. 2D to better illustrate features of the stent manufacturing assembly 200. After the inner cutout portion 202a, the stent portion 204a, and the outer cutout portion 206a are folded around the mandrel 220, the first long edge of the stent portion 204a may be welded to the second long edge of the stent portion 204a at welding zones. The welding zones of the stent portion 204a of the patterned metal sheet 204 may correspond to gaps 218 in the outer cutout portion 206a of the outer shield 206. When a first long edge 216a and a second long edge 216b of the outer cutout portion 206a are folded around the patterned metal sheet 204, some portions 219a of the first long edge 216a may meet (or be a short distance away from) the second long edge 216b along the length of the outer cutout portion 206a while other portions 219b along the length of the outer cutout portion 206a may include gaps 218 between the first long edge 216a and the second long edge 116b. As stated above, the gaps 218 between the first long edge 216a and the second long edge 216b may provide, for example, access to portions of the patterned metal sheet 204 for injection of argon gas, illumination, and laser welding at specific weld zones. The inner alignment portion 202b, the stent sheet alignment portion 204b, and the outer alignment portion 206b remains stationary in, for example, a stent rolling mechanism.

Figure 2F:
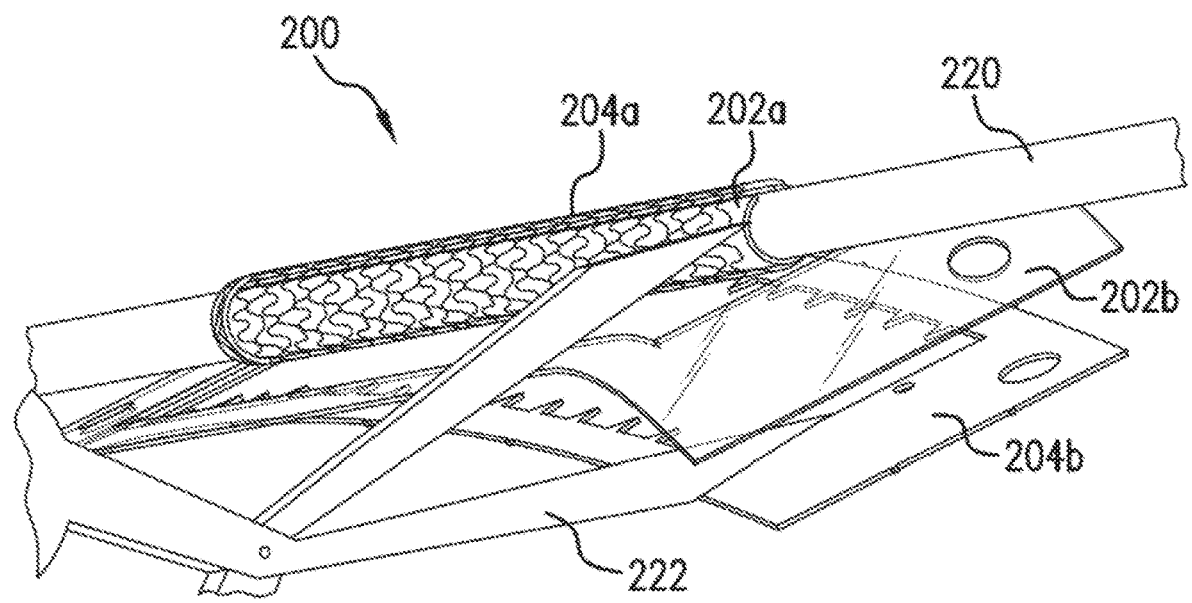
FIG. 2F shows a further step in manufacturing a stent using a stent manufacturing assembly where the inner shield is cut away.

FIG. 2F shows a further step in manufacturing a stent using a stent manufacturing assembly 200 where the inner shield 202 is cut away from the inner cutout portion 202a. In this step, the outer shield 206 has been removed from the stent manufacturing assembly 200. The stent sheet alignment portion 204b of the patterned metal sheet 204 is also removed while the now-welded stent portion 204a of the patterned metal sheet 204 forms a tubular stent around the mandrel 220. To remove the inner alignment portion 202b, a cutting tool such as, for example, scissors 222 is used to cut the inner tabs of the inner shield 202 and separate the inner cutout portion 202a from the inner alignment portion 202b, which is then discarded. However, one of skill in the art will recognize that any suitable cutting tool may be used to separate the inner cutout portion 202a from the inner alignment portion 202b. The tubular stent formed from the stent portion 204a may be slid off the mandrel with (or without) the inner cutout portion 202a.

FIG. 3A-3C show a mandrel 320 used to manufacture a stent. As described above, the mandrel 320 may include any suitable diameter between about 1 mm and about 2 mm and a length between about 50 mm and about 200 mm. For example, as shown in FIG. 3A, the mandrel 320 includes a diameter of about 1.3 mm and a length of about 100 mm.

Figure 4A:
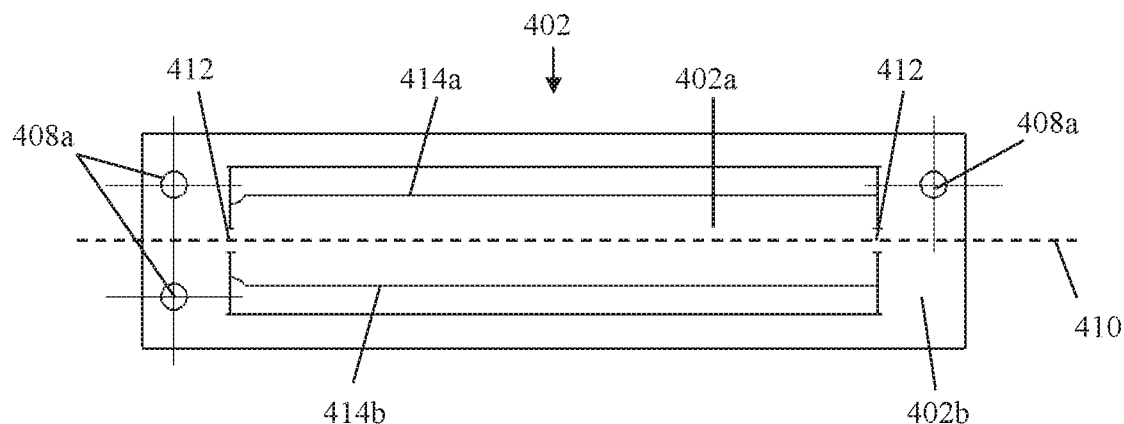
FIGS. 4A and 4B show an inner shield of a stent manufacturing assembly.
Figure 4B:
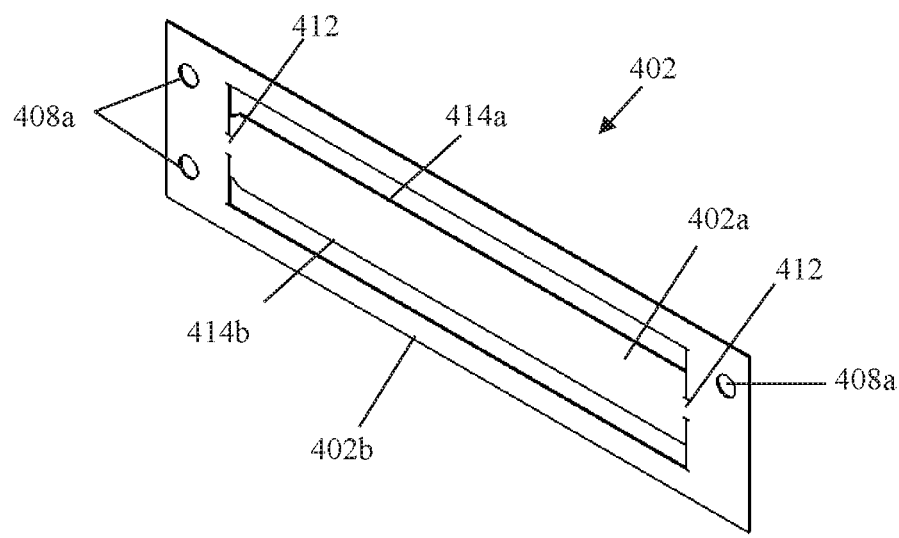

FIGS. 4A and 4B show an inner shield 402 of a stent manufacturing assembly. The inner shield 402 is substantially similar to the inner shields described above and includes an inner cutout portion 402a, an inner alignment portion 402b, and at least two inner tabs 412 connecting the inner cutout portion 402a to the inner alignment portion 402b. Similar to the inner shields described above, the cutout portion 402a of the inner shield includes a first long edge 414a and a second long edge 414b that are substantially parallel to the longitudinal axis 410 of the inner cutout portion 402a. When the inner cutout portion 402a is folded around a mandrel, the first long edge 414a may meet the second long edge 414b.

The inner alignment portion 402b includes inner alignment holes 408a. The inner alignment holes 408a may be used to align the inner shield 402 with the patterned metal sheet and outer shield by inserting an alignment pin through each of the inner alignment holes 408a and also through alignment holes in the patterned metal sheet and the outer shield.

Figure 5A:
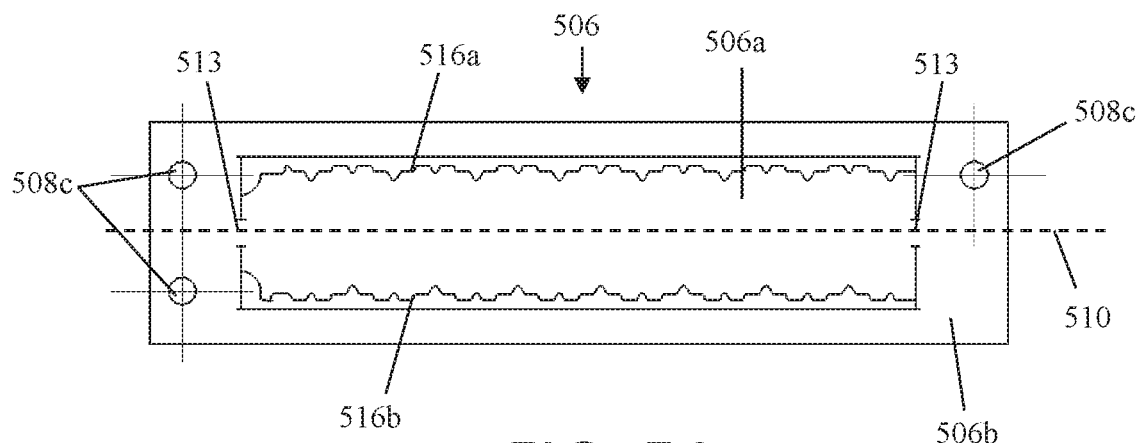
FIGS. 5A and 5B show an outer shield of a stent manufacturing assembly.
Figure 5B:
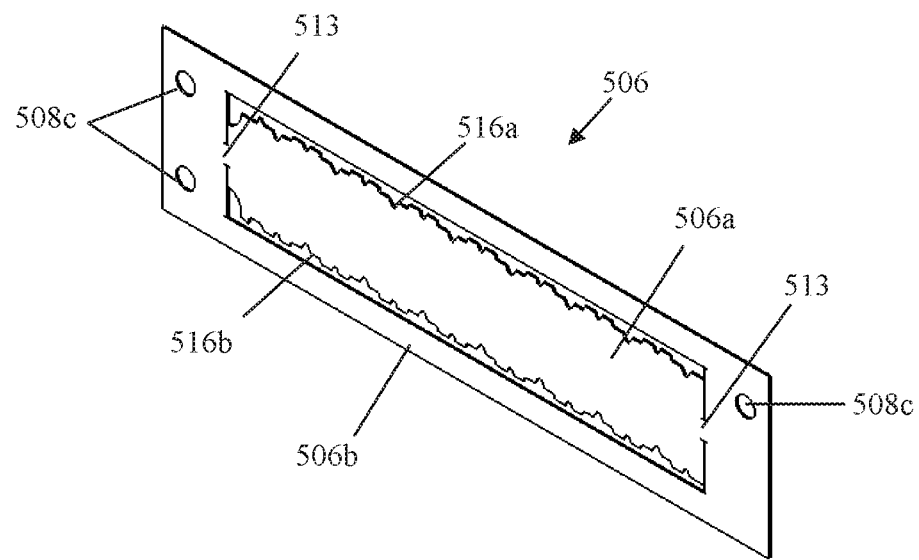

FIGS. 5A and 5B show an outer shield 506 of a stent manufacturing assembly. The outer shield 506 is substantially similar to the outer shields described above and includes an outer cutout portion 506a, an outer alignment portion 506b having outer alignment holes 508c, and at least two outer tabs 513 connecting the outer cutout portion 506a to the outer alignment portion 506b.

Similar to the outer shields described above, the outer cutout portion 506a includes a first long edge 516a and a second long edge 516b having a toothed or jagged configuration along the longitudinal length of the outer cutout portion 506a defined along the longitudinal axis 510 of the outer shield 506. When the outer cutout portion 506a is folded around the patterned metal sheet, some portions of the first long edge 516a may meet the second long edge 516b along the length of the outer cutout portion 506a while other portions along the length of the outer cutout portion 506a may include gaps between the first long edge 516a and the second long edge 516b. The gaps between the first long edge 516a and the second long edge 516b may provide, for example, access to portions of the patterned metal sheet for injection of argon gas, illumination, and laser welding at specific weld zones. Gaps may be defined when a valley in the first long edge 516a aligns with a valley in the second long edge 516b. Similarly, the first long edge 516a may be a short distance from or in contact with the second long edge 516b when a peak of the first long edge 516a aligns with a peak of the second long edge 516b. The specific shape of the first long edge 516a and second long edge 516b will be defined by the points at which laser welding, illumination, or argon gas injection will occur, and it is preferred to have correspondence therewith.

Figure 6A:
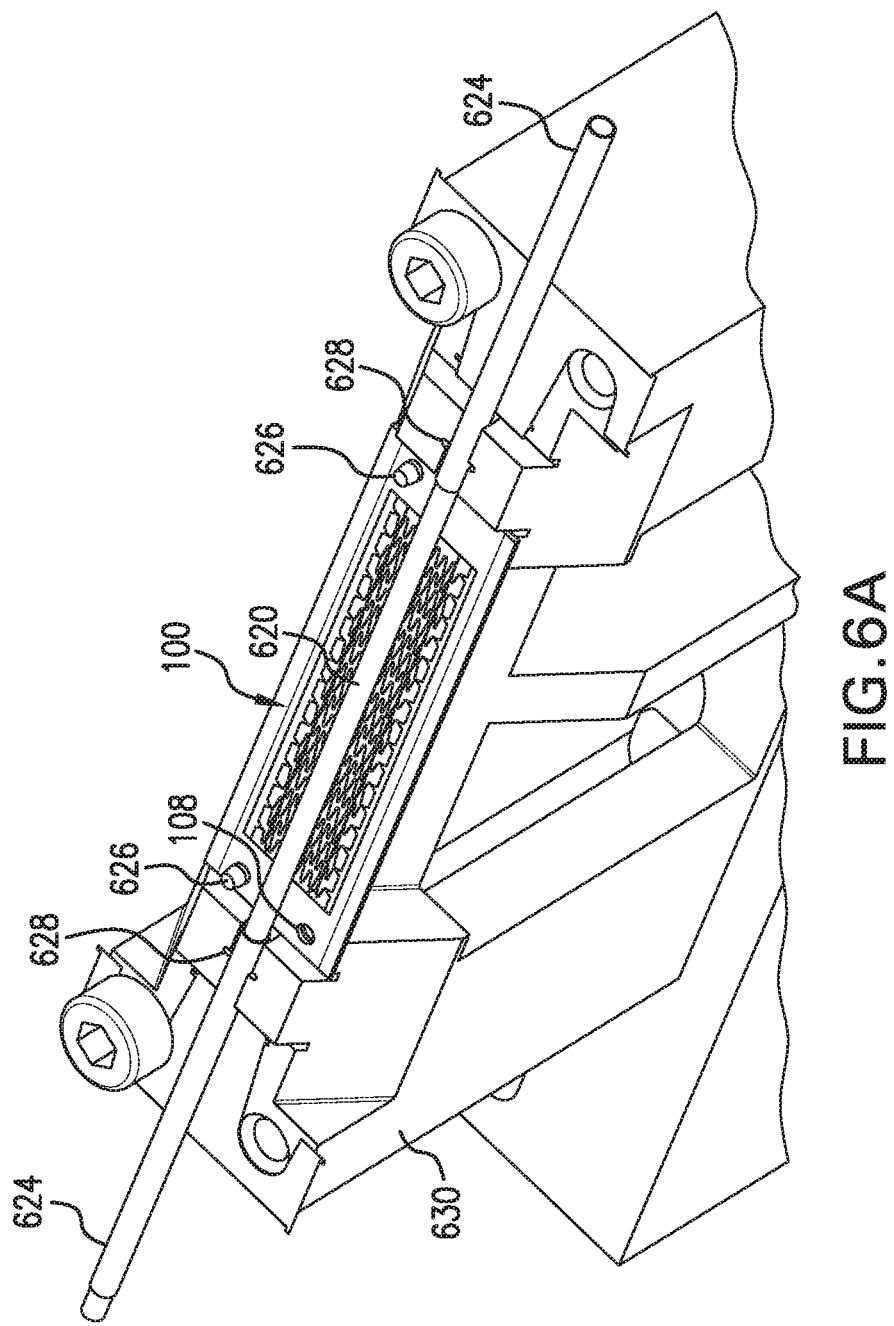
FIG. 6A shows a stent manufacturing assembly aligned on a stent rolling device with alignment pins.

FIG. 6A shows a stent manufacturing assembly 100 aligned on a stent rolling device 630 with alignment pins 626. The stent manufacturing assembly 100 may include the inner shield 102, patterned metal sheet 104, and outer shield 106 as described above in a layered configuration. When the stent manufacturing assembly 100 is placed in the stent rolling mechanism 630, the alignment holes 108 of the stent manufacturing assembly 100 may be aligned with alignment pins 626 of the stent rolling mechanism 630. The alignment pins 626 and corresponding alignment holes 108 may constrain the stent manufacturing assembly from moving during the rolling and welding of the patterned metal sheet into a tubular stent.

The stent rolling mechanism 630 may further include grooves 628 that are configured to hold the mandrel 620 securely in place while the stent manufacturing assembly 100 is rolled and welded. In the event that the groove 628 is too large, a tube 624 may be slid over the mandrel 620 on either end to increase the diameter of the mandrel 620 so that the mandrel 620 will tightly fit into the groove 628. The tube may be made of, for example, polytetrafluoroethylene (PTFE) or another suitable polymer or metal.

Figure 6B:
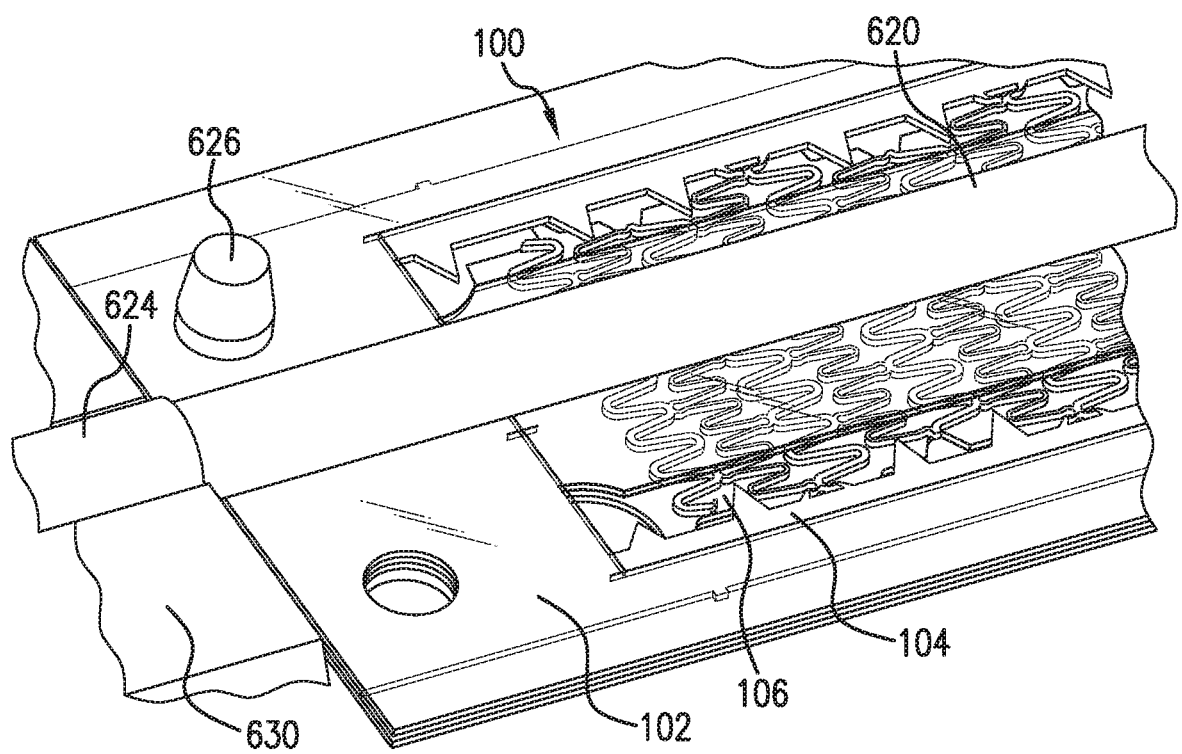
FIG. 6B shows an enlarged view of the stent manufacturing assembly on a stent rolling device.

FIG. 6B shows an enlarged view of the stent manufacturing assembly 100 on a stent rolling device 630. In particular, FIG. 6B shows one part of the stent manufacturing assembly 100 loaded into the stent rolling mechanism 630 where one alignment hole 108 of the stent manufacturing assembly 100 is aligned with an alignment pin 626 of the stent rolling mechanism 630. As stated above with respect to FIG. 6A, after loading into the stent rolling mechanism 630, the stent manufacturing assembly 100 may be rolled around the mandrel 620. The stent manufacturing assembly 100 may be held in place by, e.g., a manual device or an automatic folder, so that the patterned metal sheet may be welded to form a tubular stent. In an embodiment, the stent manufacturing assembly 100 may be held in place any time before and during welding.

FIG. 7 shows a flow diagram for a method 700 of manufacturing a stent using a stent manufacturing assembly. At 702, the method includes providing a stent manufacturing assembly comprising a patterned metal sheet having a sheet alignment portion and a stent portion, an inner shield having an inner alignment portion and an inner cutout portion, and an outer shield having an outer alignment portion and an outer cutout portion. The method may further comprise positioning the patterned metal sheet on the outer shield, such that a first side of the patterned metal sheet contacts the outer shield to protect the first side of the patterned metal sheet from contacting a stent rolling mechanism. The method may further include positioning the inner shield on a second side of the patterned metal sheet to protect the second side of the patterned metal sheet from contacting a mandrel. The method may further comprise loading the stent manufacturing assembly into a stent rolling mechanism by aligning one or more alignment holes in each of the layers (i.e., inner shield, patterned metal sheet, and outer shield) of the stent manufacturing assembly with alignment pins in the stent rolling mechanism.

At 704, the method may further comprise rolling the inner cutout portion, the stent portion, and the outer cutout portion around the mandrel. In particular, the method may further include deforming the stent portion with the inner cutout portion and the outer cutout portion around the mandrel. The method may further include holding the rolled stent portion, inner cutout portion, and outer cutout portion together such that a first long edge of the stent portion may be in contact with or proximate to a second long edge of the stent portion for further processing steps, such as, e.g., welding of the first long edge and the second long edge.

At 706, the method may further comprise welding a first long edge of the stent portion to a second long edge of the stent portion to form a tubular stent. The first long edge may be welded at specific weld zones or in its entirety to the second long edge. The method may further include spot welding using any suitable number of spot welds. In an embodiment, the method may further include five to forty spot welds along the length of the stent portion.

At 708, the method may further include removing the tubular stent from the mandrel. The tubular stent may be slid off the mandrel with the outer cutout portion and/or the inner cutout portion. In an embodiment, the method includes separating the inner cutout portion from the inner alignment portion using a cutting mechanism, such as, e.g. scissors. In yet another embodiment, the method further includes separating the outer cutout portion from the outer alignment portion using a cutting mechanism, such as, e.g. scissors.

In another embodiment, the method includes removing the outer shield from the tubular stent. The outer shield may be peeled off of the second side of the stent portion (corresponding to the outer surface of the resulting stent) after welding or after the tubular stent has been removed from the mandrel. In yet another embodiment, either concurrently with or after the tubular stent is removed from the mandrel, the inner shield may be removed from the mandrel.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the invention disclosed herein. All references cited herein are incorporated by reference in their entirety and made part of this application.

What is claimed is:

1. A stent manufacturing assembly comprising:
   an outer shield having an outer cutout portion and an outer alignment portion;
   a patterned metal sheet positioned on the outer shield, said patterned metal sheet having a stent portion and a stent alignment portion; and
   an inner shield having an inner cutout portion and an inner alignment portion, said inner shield positioned on the patterned metal sheet.

2. The stent manufacturing assembly of claim 1, wherein the inner alignment portion of the inner shield further comprises one or more alignment holes.

3. The stent manufacturing assembly of claim 1, wherein the inner cutout portion further comprises flat long edges.

4. The stent manufacturing assembly of claim 1, wherein the inner shield comprises tabs connecting the inner cutout portion to the inner alignment portion.

5. The stent manufacturing assembly of claim 1, wherein the outer shield comprises tabs connecting the outer cutout portion to the outer alignment portion.

6. The stent manufacturing assembly of claim 1, wherein the inner shield is selected from the group comprising: polytetrafluoroethylene (PTFE) and silicon.

7. The stent manufacturing assembly of claim 1, wherein the outer shield is selected from the group comprising: polytetrafluoroethylene (PTFE) and silicon.

8. The stent manufacturing assembly of claim 1, wherein the inner shield and the outer shield are disposable.

9. The stent manufacturing assembly of claim 1, wherein the inner shield comprises a thickness of about 0.1 mm.

10. The stent manufacturing assembly of claim 1, wherein the outer shield comprises a thickness of about 0.1 mm.

11. The stent manufacturing assembly of claim 1, wherein the outer cutout portion comprises toothed long edges.

12. The stent manufacturing assembly of claim 1, wherein the patterned metal sheet comprises one or more alignment holes.

13. The stent manufacturing assembly of claim 1, wherein the outer alignment portion comprises one or more alignment holes.

14. The stent manufacturing assembly of claim 1, further comprising a mandrel.

15. The stent manufacturing assembly of claim 14, wherein the mandrel comprises platinum, gold, stainless steel, or a platinum-iridium alloy.

16. The stent manufacturing assembly of claim 14, wherein the mandrel comprises a diameter between 1 mm and 2 mm.

17. The stent manufacturing assembly of claim 14, wherein the mandrel comprises a diameter of about 1.3 mm.

18. The stent manufacturing assembly of claim 14, wherein the mandrel comprises a length between 50 mm and 200 mm.

19. The stent manufacturing assembly of claim 14, wherein the mandrel comprises a length of about 100 mm.

20. The stent manufacturing assembly of claim 1, wherein the patterned metal sheet comprises a coating.

21. The stent manufacturing assembly of claim 20, wherein the coating comprises a therapeutic agent.

22. The stent manufacturing assembly of claim 21, wherein the therapeutic agent is an anti-proliferative agent.

23. A method of manufacturing a stent comprising:
   providing a stent manufacturing assembly comprising an outer shield having an outer cutout portion and an outer alignment portion, a patterned metal sheet disposed on the outer shield, said patterned metal sheet having a stent portion and a stent alignment portion; and an inner shield having an inner cutout portion and an inner alignment portion, said inner shield disposed on the patterned metal sheet;
   rolling the inner cutout portion, the stent portion, and the outer cutout portion around a mandrel;
   welding a first long edge of the stent portion to a second long edge of the stent portion to form a tubular stent; and
   removing the tubular stent from the mandrel.

24. The method of claim 23, further comprising removing the outer shield from the tubular stent.

25. The method of claim 24, further comprising removing the inner shield from the tubular stent.

26. The method of claim 25, wherein removing the inner shield comprises cutting a tab connecting the inner cutout portion to the inner alignment portion.

27. The method of claim 23, further comprising loading the stent manufacturing assembly into a stent roller.

28. The method of claim 27, wherein the inner alignment portion, the sheet alignment portion, and the outer alignment portion each comprise alignment holes, the method further comprising aligning the alignment holes with one or more alignment pins on the stent roller.

29. The method of claim 23, further comprising polishing the tubular stent.

30. The method of claim 29, wherein polishing is performed by electropolishing.

* * * * *